(12) United States Patent
Lin

(10) Patent No.: US 7,147,319 B2
(45) Date of Patent: Dec. 12, 2006

(54) EYEWEAR PROVIDING COLORED LIGHT THERAPY

(76) Inventor: Ta-Wei Lin, 7Fl., No. 55, Lane 100, Tun-Hwa South Road, Sec. 1, Taipei (TW)

( * ) Notice: Subject to any disclaimer, the term of this patent is extended or adjusted under 35 U.S.C. 154(b) by 0 days.

(21) Appl. No.: 11/023,164

(22) Filed: Dec. 28, 2004

(65) Prior Publication Data

US 2006/0007390 A1    Jan. 12, 2006

(30) Foreign Application Priority Data

Jul. 8, 2004   (TW) ............................... 93120415 A

(51) Int. Cl.
   *G02C 11/02* (2006.01)
(52) U.S. Cl. ........................... 351/51; 351/52; 351/158
(58) Field of Classification Search .................. 351/41, 351/51, 52, 158, 200, 203, 245
   See application file for complete search history.

(56) References Cited

U.S. PATENT DOCUMENTS 4,254,451 A * 3/1981 Cochran, Jr. ................. 362/103

6,857,739 B1 * 2/2005 Watson ........................ 351/158

FOREIGN PATENT DOCUMENTS

| FR | 2554605 | * | 10/1985 | .................. 351/158 |
| JP | 2-181722 | * | 7/1990 | .................. 351/51 |

* cited by examiner

*Primary Examiner*—Huy Mai
(74) *Attorney, Agent, or Firm*—Arent Fox PLLC

(57) ABSTRACT

An eyewear for administering colored light therapy comprising an eyepiece; a frame element for supporting said eyepiece in a position exposing the inner surface thereof to the wearer of said eyewear; and a plurality of light-generating units on said frame element each for generating a light of controlled color and intensity and illuminating onto said inner surface of said eyepiece for display of said generated light to the eyes of said wearer. The eyewear provides a colored light therapy display area close to the eyes of the wearer allowing for convenient implementation of the therapy almost anywhere. The eyewear is also easy to be converted into an eyewear of fun for entertainment purposes by the replacement of a transparent eyepiece.

21 Claims, 3 Drawing Sheets

EYEWEAR PROVIDING COLORED LIGHT THERAPY

BACKGROUND OF THE INVENTION

1. Field of the Invention

The present invention relates in general to eyewear and, in particular, to an eyewear for providing light therapy for the wearer thereof. More particular, the present invention relates to an eyewear for providing light therapy to the wearer thereof by the provision of colored light at the control of the wearer.

2. Description of the Related Art

Light therapy, or, chromotherapy, is a science that uses different colors to change and maintain vibrations to the body so that the frequency that signifies health and harmony can be applied to the body either physically or through definite exposure of light rays. Healing by means of color was probably the first type of therapy used by man because it was nature's own method.

One typical such therapy can, for example, be practiced to assist sleep on persons undertaking long distance travels. For example, business people flying more than ten hours in intercontinental flights usually find themselves difficult to get into sleep when they should or want. Confined seating space in modern airliners is not the only reason for an air traveler's sleep difficulties. Time zone crossing further complicates the situation as a traveler's biological clock becomes disturbed. A colored light therapy can be helpful for air travelers via peaceful calm down of minds using a display of colored lights.

Further, there have been various medical research results confirming the effect of light of different colors on the human body. For example, red light is believed to assist blood circulation, while blue brings calmness to certain people It has been necessary for colored light therapy to be performed in dedicated space and environment. Color-lighting schemes designed for the desired colored light therapy need to be performed in a dedicated room equipped with suitable lighting equipments and adequate surrounding backgrounds. A colored light therapy room would normally require to be a substantially confined and separate space in order to not constitute interference to any other person nearby. Set up of such a colored light therapy environment is therefore relatively costly. A space/environment set up for colored light therapy, due to its required lighting specifications, is therefore limited in use.

SUMMARY OF THE INVENTION

It is therefore an object of the present invention to provide an eyewear for colored light therapy that does not require a dedicated space/environment for the implementation of the colored light therapy sessions.

It is another object of the present invention to provide an eyewear for colored light therapy that is inexpensive to make.

It is yet another object of the present invention to provide an eyewear for colored light therapy that can be converted for non-therapy entertainment applications with ease and convenience.

The present invention achieves the above and other objects of the invention by providing an eyewear comprising an eyepiece; a frame element for supporting said eyepiece in a position exposing the inner surface thereof to the wearer of said eyewear; and a plurality of light-generating units on said frame element each for generating a light of controlled color and intensity and illuminating onto said inner surface of said eyepiece for display of said generated light to the eyes of said wearer.

The present invention also provides a colored light therapy eyewear comprising a frame element for supporting an eyepiece in a position exposing the inner surface thereof to the wearer of said eyewear; and a plurality of light-generating units on said frame element each for generating a light of controlled color and intensity and illuminating onto said inner surface of said eyepiece for display of said generated light to the eyes of said wearer.

DETAILED DESCRIPTION OF THE PREFERRED EMBODIMENTS

Figure 1:
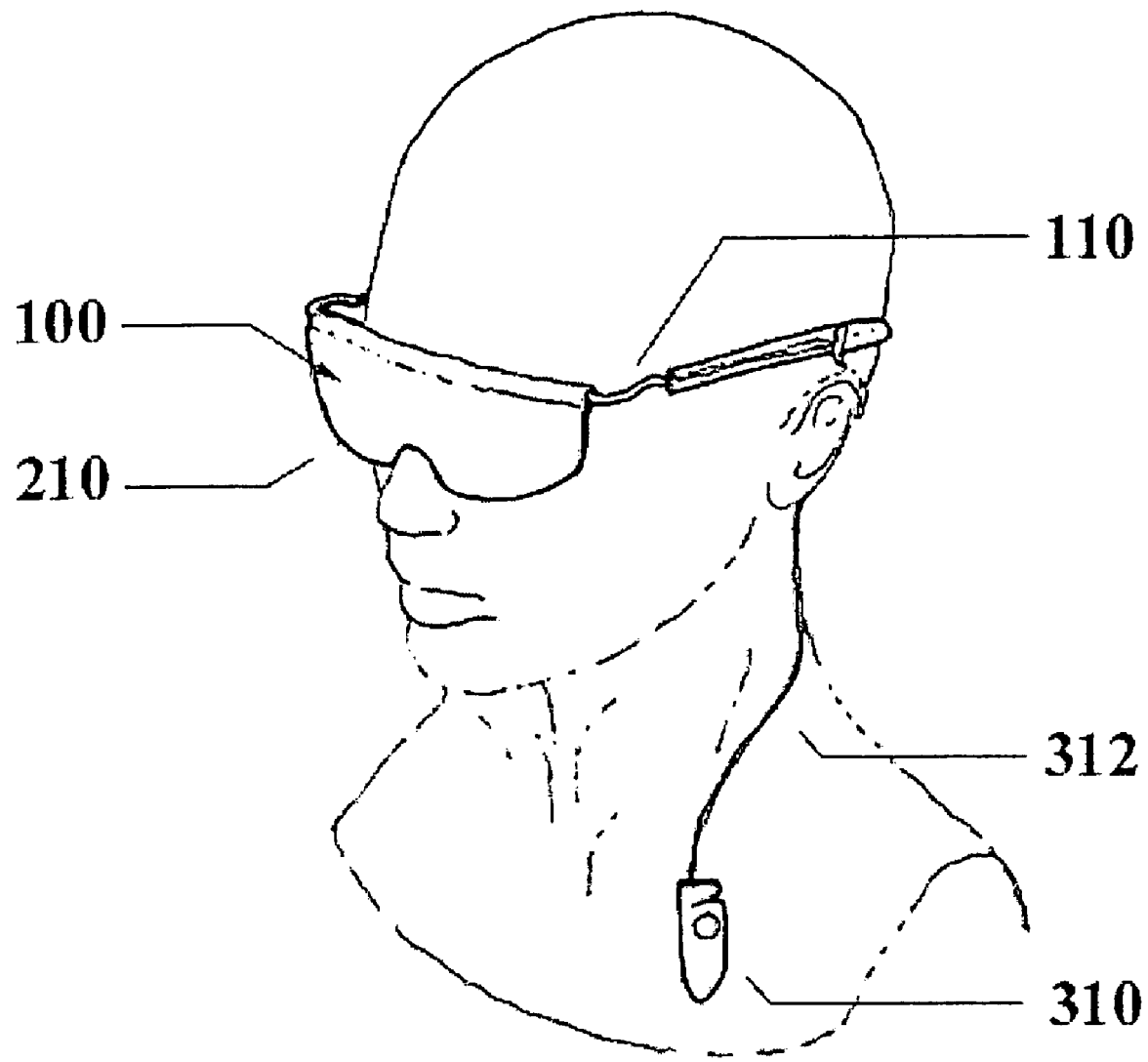
FIG. 1 is a perspective view of the preferred embodiment of the eyewear of the present invention.

FIG. 1 is a perspective view of a preferred embodiment of the eyewear of the present invention. Preferably, an eyewear of the present invention may substantially take the physical form of any typical spectacles or goggles. Such an eyewear is typically worn in much the same way by the wearer either for the purpose of colored light therapy or for fun in entertainment and leisure occasions.

A preferred embodiment of the eyewear of the present invention as depicted by reference numeral 100 in FIG. 1 comprises an eyepiece 210 and a frame 110. The two components are assembled together in a fixed manner for wearing by the wearer. They can also be disassembled from each other so that eyepieces of different colors, shapes and/or transparency/opaqueness can be interchanged for different purposes and wearing occasions of the eyewear.

Figure 2:
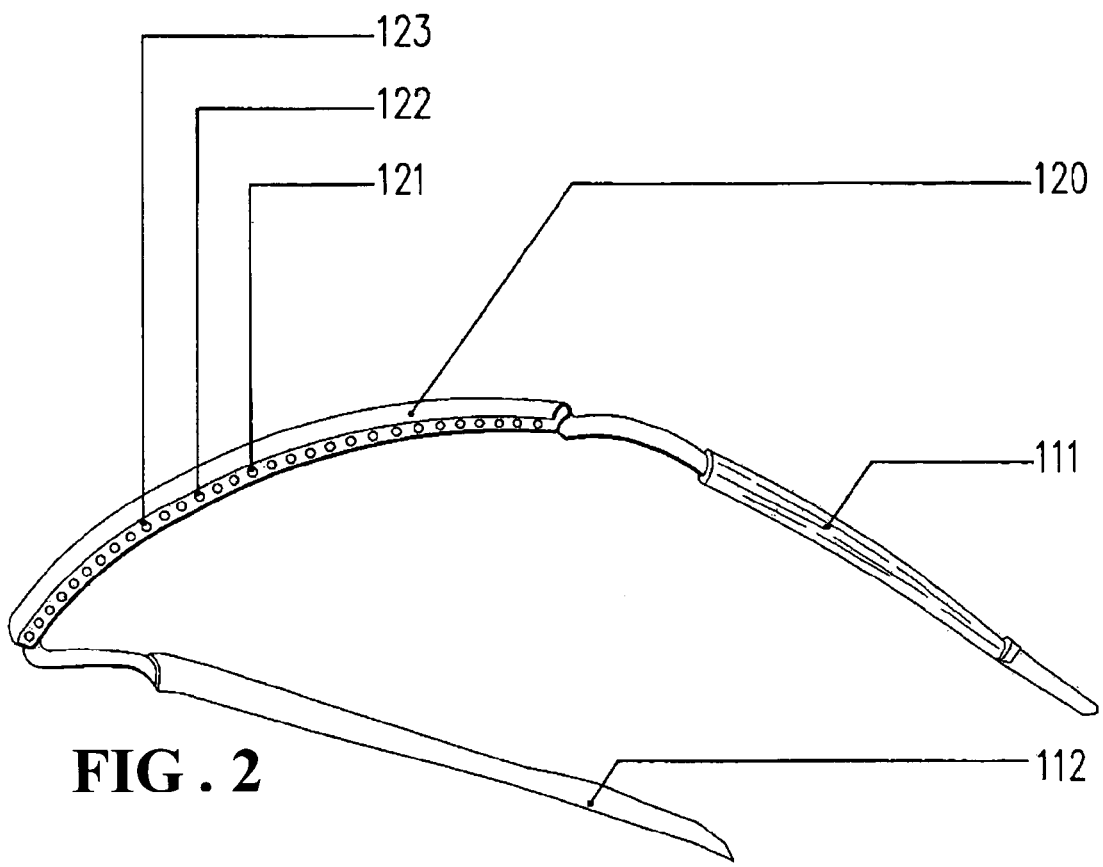
FIG. 2 is a perspective view of the frame for the eyewear of FIG. 1.
Figure 3:
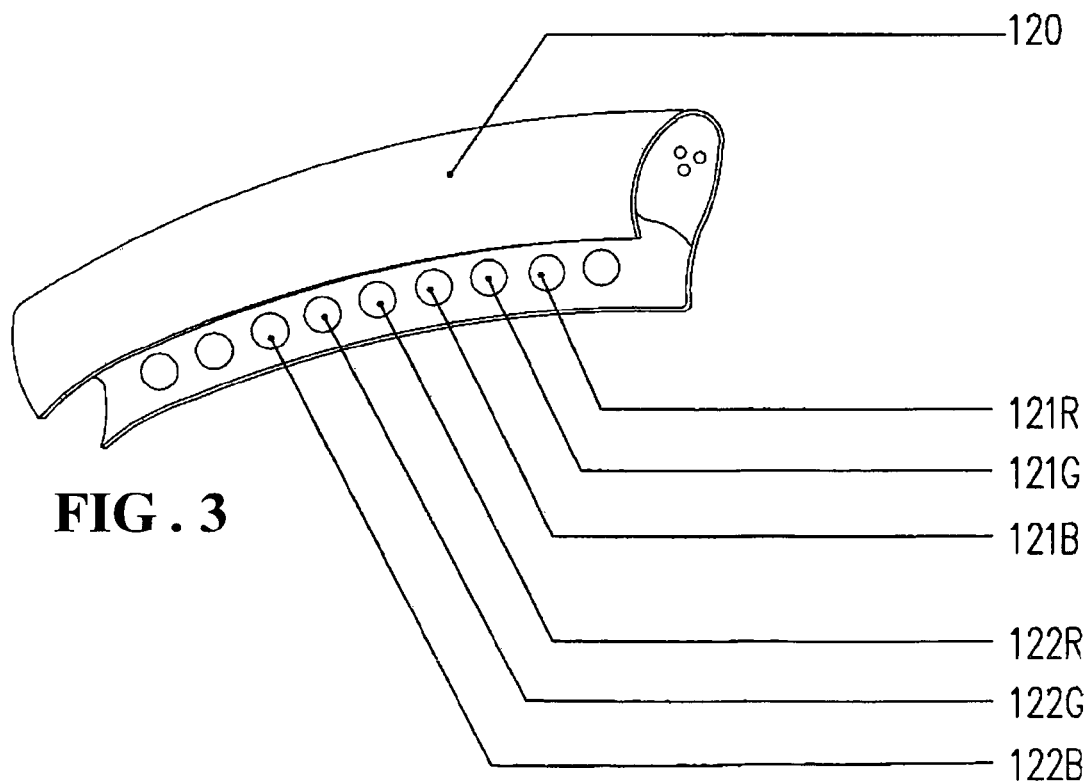
FIG. 3 shows in detail the arrangement of light-generating units on the frame of FIG. 2.

In order to implement light generation of the purpose of either colored light therapy or leisure, a light generator comprising a plurality of light generating means is included in the frame 110 of the eyewear. FIGS. 2 and 3 depict a preferred embodiment of the arrangement of such a system of light-generating means, which will be described in more detail in the following paragraphs.

In one embodiment of the eyewear of the present invention, as is illustrated in FIG. 1, the eyewear 100 further includes a lighting control means 310 connected to the frame 110 via, for example, a section of electrical wiring 312. In this described embodiment, the lighting control means 310 houses the power source, preferably a battery, that supplies lighting power to the light-generating means installed in the frame 110. The lighting control means 310 can also house a switch means for wearer's control of the turning on and off and the selection of the lighting scheme to be implemented by the eyewear. Though, as anyone skilled in the art can comprehend, the lighting on/off and lighting scheme selection switch means can be installed to the frame 110 itself instead of being in the lighting control means such as means 310.

Perspective view of FIG. 2 illustrates an embodiment of the frame 110 for the eyewear 100 of FIG. 1. The frame 110 comprises an eyepiece supporting beam 120, and a pair of earpieces 111 and 112 connected thereto via hinge means at the two opposite ends of the beam. The hinged connection of the two ear pieces 111 and 112 to the beam 120 can be implemented in much the same method as found in conventional eyewear such as for vision correction and sun shading.

A light generating means comprising a plurality of light-generating units 121, 122, . . . and 123 are preferably installed to the beam 120 of the frame 110 each having light-emanating surfaces 130 facing toward the downward direction of the frame 110 of FIG. 2. Each of the light-generating units 121, 122, . . . and 123 are arrayed along the generally elongated body of the beam 120 and are, preferably, populated evenly along the entire length of the beam 120.

FIG. 3 shows in detail the arrangement of light-generating units 121, 122, . . . and 123 on the frame 120 of FIG. 2. Preferably, each of the light-generating units 121, 122 and 123 are built up utilizing light-emitting diodes (LED). LED's of the three prime colors red, green and blue are commercially available at relatively inexpensive costs. One red, one green and one blue LED can be included in each of the light-generating units 121, 122, . . . and 123 and excited under control so that each of the light-generating units can generate a light of desired color and intensity.

All the light-generating units 121, 122, . . . and 123 of the light-generating means such as illustrated in the detailed perspective view of FIG. 3 can be grossly connected in a power supply network so that they can either be excited to generate light of the same color and intensity or, alternatively, they can also be controlled in different light generating schemes that each of them produces light with correspondingly different color and/or intensity. The control is dependent on the purpose of the use of the inventive eyewear, either for colored light therapy or leisure and fun. Depending on the control circuitry included for the eyewear, light generated by each of the units 121, 122, . . . and 123 can be more than thousands of colors and the intensity can be from soft to strong. This is possible, as is comprehensible to those skilled in the art, in the light-generating unit 122 of FIG. 3 for example, via separate control of each of the prime color LEDs 122R (for the red prime color), 122G (green) and 122B (blue). Either straightforward sequential digital electronics or microcontroller-based system can be used to implement this color and intensity control for the light-generating units installed in the eyewear.

Figure 4:
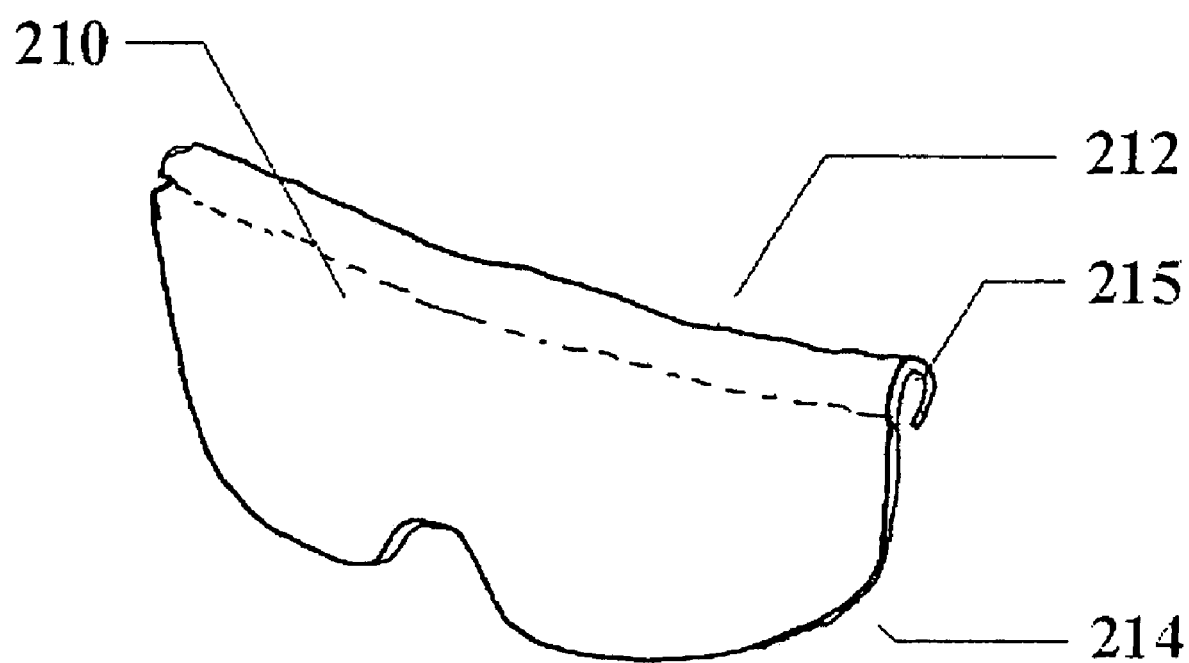
FIG. 4 is perspective view illustrating the eyepiece for the eyewear of FIG. 1.

FIG. 4 is a perspective view illustrating a preferred embodiment of the eyepiece 210 for the eyewear 100 of FIG. 1. Such an eyepiece 210 can be matchedly assembled with the frame 110, for example, as depicted in FIGS. 2 and 3. To be assembled to the frame 110, the eyepiece 210 preferably comprises an eyeplate 214 and a frame-clamping means 212. The eyeplate 214 and the corresponding frame-clamping means 212 can be manufactured as an integral part or, alternatively, they can be two separate components assembled fixedly together. Preferably, the frame-clamping means 212 of the eyeplate 210 is equipped with a frame-insertion space 215 extending along substantially all the width of the eyepiece 210. The frame-insertion space 215 serves to receive in a firm and secured manner the beam 120 of the frame 110 of the inventive eyewear. This can be achieved for the eyepiece 210 of FIG. 4 and the frame 110 of FIGS. 2 and 3 by pushing the beam 120 of the frame 110 into the frame-insertion space 215 of the frame-clamping means 212 via the opening facing toward the downward of the eyewear.

Eyeplate 214 of the eyepiece 210 can be of various opaque and/or transparency nature. For example, for colored light therapy, a wearer can select to assemble to the frame 110 an eyepiece 210 with an opaque eyeplate 214 of a desired color. When assembled and worn, the eyewear 100 effectively constitutes a display device set up in close proximity to the eyes of the wearer. As the light generating means to be described in the following paragraphs is turned on to generate light or lights of different colors and intensity under controlled color- and intensity-changing schemes, the inner surface of the eyepiece 210 directly facing toward the eyes of the wearer becomes a display screen for administering colored light therapy sessions to the wearer.

In a preferred embodiment of the present invention, an eyewear may have an eyepiece 210 equipped with an eyeplate 214 having a dark, black for example, external surface and a bright, preferably white, internal surface. The bright, or white, internal surface of the eyeplate 214 serves to reflect the prescribed lights as administered by the light-generating units 121, 122, . . . and 123 of the light-generating means into the wearer's eyes without altering their originally generated colors. The dark external surface of the eyeplate 214, on the other hand, can block the lights generated onto the internal surface from escaping. As such, the generated lights are utilized with high efficiency, while the wearer can undertake an effective session without interfering with others nearby.

Alternatively, an eyepiece 210 with a transparent eyeplate can be used for non-chromotherapy occasions such as, for example, in parties and other entertainment purposes. As opposed to the opaque eyeplate suitable for colored light therapy sessions, a transparent eyeplate allows the wearer of the inventive eyewear to look through the eyepiece so that the wearer has not eyesight obstruction. This allows the inventive eyewear to be worn in parties and other leisure instances where the light-generating means can also be turned on to introduce a fancy and interesting effect of light display in the face area of the wearer. For example, a wearer wearing the inventive eyewear of the present invention with a transparent eyepiece and with the light-generating means turned on can be the focus of a night party of a night parade.

Further, without the light-generating means of the inventive eyewear turned on, a sun-shading eyepiece can be assembled to the frame 110 so that the eyewear effectively becomes a sunglass. This provides another usefulness of the eyewear of the present invention in addition to the colored light therapy and entertainment applications described above.

Since the inner display screen of the eyepiece 210 is very close to the eyes of the wearer, the overall suitable light intensity necessary for the implementation of a colored light therapy session can be relatively small as compared to similar colored light therapy sessions conducted in a room environment. As a result of this space and power (required to light the LED-based light-generating units) efficiency, colored light therapy becomes convenient and inexpensive and can be performed at various locations at almost anytime without constituting interference to others nearby.

As an example, the eyewear of the present invention can be particularly useful for business travelers spending long hours in intercontinental flights. Whenever a flyer decides it's time to sleep during a long flight, he or she can put on an eyewear of the present invention and prescribe him- or herself a sleep-assisting coloring light scheme. Implementation of such a colored light therapy session in the confined and closely-packed seating area will not interfere with even the passenger right next by.

Further, since the change and replacement of any desired eyepiece for the eyewear is very simple and easy, the eyewear can be converted among the possible applications (colored light therapy, entertainment and sun-shading utility) virtually instantly.

While the above is a full description of the specific embodiments, various modifications, alternative constructions and equivalents may be used. For example, instead of a two-part implementation involving a frame and an eyepiece for a colored light therapy eyewear of the present invention, one with integral frame and eyepiece is also possible. Therefore, the above description and illustrations should not be taken as limiting the scope of the present invention which is defined by the appended claims.

What is claimed is:

1. An eyewear comprising:
an eyepiece;
a frame element for supporting said eyepiece in a position exposing the inner surface thereof to the wearer of said eyewear; and
a plurality of light-generating units on said frame element each for generating a light of controlled color and intensity and illuminating onto said inner surface of said eyepiece for display of said generated light to the eyes of said wearer,
wherein each of said plurality of light-generating units comprises at least one red light-generating means, at least one green light-generating means and at least one blue light-generating means.

2. The eyewear of claim 1, wherein said frame element comprises:
a pair of ear pieces; and
an elongated eyepiece-supporting beam flexibly connected to each of said pair of ear pieces at each of the opposite ends thereof.

3. The eyewear of claim 1, wherein said at least one red, green and blue light-generating means are red, green and blue light-emitting diodes respectively.

4. The eyewear of claim 1, wherein each of said plurality of light-generating units generates light of substantially the same color.

5. The eyewear of claim 1 wherein each of said plurality of light-generating units generates light of substantially the same intensity.

6. The eyewear of claim 1, wherein said eyepiece is a non-transparent eyepiece having a substantially white internal surface for reflecting said generated light illuminated thereon into the eyes of said wearer.

7. The eyewear of claim 6, wherein said eyepiece further has a dark external surface for blocking said generated light illuminated thereon from escaping from said internal surface.

8. The eyewear of claim 1, wherein said eyepiece is an opaque eyepiece for reflecting said generated light illuminated thereon into the eyes of said wearer.

9. The eyewear of claim 1, wherein said eyepiece is a partially-transparent eyepiece for partially reflecting said generated light illuminated thereon into the eyes of said wearer and allowing partial passage of said generated light illuminated thereon.

10. The eyewear of claim 1, wherein said eyepiece is a transparent eyepiece for total passage of said generated light illuminated thereon without reaching to the eyes of said wearer.

11. A colored light therapy eyewear comprising:
a frame element for supporting an eyepiece in a position exposing the inner surface thereof to the wearer of said eyewear; and
a plurality of light-generating units on said frame element each for generating a light of controlled color and intensity and illuminating onto said inner surface of said eyepiece for display of said generated light to the eyes of said wearer,
wherein each of said plurality of light-generating units comprises at least one red light-generating means, at least one green light-generating means and at least one blue light-generating means.

12. The eyewear of claim 11, wherein said frame element comprises:
a pair of ear pieces; and
an elongated eyepiece-supporting beam flexibly connected to each of said pair of ear pieces at each of the opposite ends thereof.

13. The eyewear of claim 11, wherein said at least one red, green and blue light-generating means are red, green and blue light-emitting diodes respectively.

14. The eyewear of claim 11, wherein each of said plurality of light-generating units generates light of substantially the same color.

15. The eyewear of claim 11, wherein each of said plurality of light-generating units generates light of substantially the same intensity.

16. The eyewear of claim 11, wherein said eyepiece is a non-transparent eyepiece having a substantially white internal surface for reflecting said generated light illuminated thereon into the eyes of said wearer.

17. The eyewear of claim 16, wherein said eyepiece further has a dark external surface for blocking said generated light illuminated thereon from escaping from said internal surface.

18. The eyewear of claim 11, wherein said eyepiece is an opaque eyepiece for reflecting said generated light illuminated thereon into the eyes of said wearer.

19. The eyewear of claim 11, wherein said eyepiece is a partially-transparent eyepiece for partially reflecting said generated light illuminated thereon into the eyes of said wearer and allowing partial passage of said generated light illuminated thereon.

20. The eyewear of claim 11, wherein said eyepiece is a transparent eyepiece for total passage of said generated light illuminated thereon without reaching to the eyes of said wearer.

21. An eyewear comprising:
an eyepiece;
a frame element having a pair of ear pieces and an elongated eyepiece-supporting beam flexibly connected to each of said pair of ear pieces at each of the opposite ends thereof, said frame element supporting said eyepiece in a position exposing the inner surface thereof to the wearer of said eyewear; and
a plurality of light-generating units on said frame element each for generating a light of controlled color and intensity and illuminating onto said inner surface of said eyepiece for display of said generated light to the eyes of said wearer,
wherein said plurality of light-generating units comprise at least one red light-generating means, at least one green light-generating means and at least one blue light-generating means.

* * * * *